United States Patent [19]

Chevrier et al.

[11] Patent Number: 5,028,133

[45] Date of Patent: Jul. 2, 1991

[54] PROCESS AND DEVICE FOR ANALYSIS OF NONCONDUCTIVE SURFACES

[75] Inventors: Michèle Chevrier, Chatenay-Malabry; Richard Passetemps, Asnieres, both of France

[73] Assignee: Regie Nationale des Usines Renault, Boulogne Billancourt, France

[21] Appl. No.: 450,463

[22] Filed: Dec. 14, 1989

[51] Int. Cl.[5] ............................................. G01N 21/66
[52] U.S. Cl. ..................................... 356/311; 356/314
[58] Field of Search ....................... 356/311, 313, 314; 313/619, 620

[56] References Cited

FOREIGN PATENT DOCUMENTS 592518  2/1934  Fed. Rep. of Germany .
2236169 1/1975  France .
55-1543 1/1980  Japan ................................... 356/311

OTHER PUBLICATIONS

Lomdahl et al, *Analytica Chimica Acta,* vol. 148, Apr. 1, 1983, pp. 171–180.
Journal of Applies Physics, vol. 37, No. 2, Feb. 1966, pp. 574–579; P. D. Davidse et al: "Dielectric thin films trough rf sputtering" *pp. 574–575* p. 575, colonne de gauche, lignes 14–17.

*Primary Examiner*—F. L. Evans
*Attorney, Agent, or Firm*—Oblon, Spivak, McClelland, Maier & Neustadt

[57] ABSTRACT

Process of analysis of surfaces by luminescent discharge spectrometry. The current used for the creation of the discharge between the anode (3) and the cathode (20) is a high-frequency current arriving on the nonconductive sample (21) to be analyzed and being propagated there by skin effect. Application is to the determination of the quality of surface coatings.

6 Claims, 2 Drawing Sheets

PROCESS AND DEVICE FOR ANALYSIS OF NONCONDUCTIVE SURFACES

BACKGROUND OF THE INVENTION

This invention relates to a process and to a device for analysis of nonconductive surfaces —such as for example lacquers deposited on synthetic materials —by luminescent discharge spectrometry, of LDS.

The principle is already known of analysis by LDS of conductive surfaces, making it possible to have qualitative and quantitative data on the constituents of said surfaces.

The principle is based on the measurement of the luminous emission that accompanies the passage of an electric current in a gas under low pressure.

The sample to be analyzed is placed cathodically in front of an enclosure under argon, at a pressure of several mbars. The ionized argon ($Ar^+$) under potential difference of 400° to 2000° dc voltage bombards the surface of the cathode sample and breaks loose the elements that constitute it. The atoms thus freed are then excited by secondary impacts with the $Ar^{30}$ ions and the electrons of the plasma: while falling to a stable or less excited level, they emit a radiation whose wavelength is characteristic of the emitting atom and whose intensity is proportional to its concentration in the plasma.

The light emitted is continuously analyzed by a spectrometer.

The ion bombarding previously described leads to a plane and regular erosion, which makes possible the continuous examination of the layers deposited on the surface of a material.

However, this process of analysis is limited to samples that are conductive or of slight resistivity, to nonconductive layers of very slight thickness (less than 2 microns), and to plane samples with a diameter greater than 20 mm.

SUMMARY OF THE INVENTION

This invention has as an object to overcome the above limitations. It applies especially, although not exclusively, to the automobile field.

Actually, in the ever-growing quest for quality of anticorrosion protective coatings, it has become necessary to check qualitatively and quantitatively the presence of the various constitutive elements of the protective layers, as well as the absence of the undesirable products in this structure. Thus, it is known that the automobile body sheet metal pieces are successively provided with layers of phosphates, cataphoretic intermediate deposits, sealer, lacquer and varnish.

Only the quality of the coating of phosphates could be checked by LDS according to the prior process, before depositing of the following layers.

This invention makes possible the continuous study of all the above layers, and thereby to check their thickness, the distribution of the elements that constitute them, the absence of undesirable compounds of the presence of migration between the strata.

In the same way, the process of analysis of the invention makes it possible to study products of synthetic material, such as vehicle shields coated with lacquers and thus to find the homogeneity and thickness of the latter.

It is also possible to apply the preceding process to the control of the quality of glued windshields, particularly by checking the property of the glass support at its edge its thickness and the nature of the bond resulting from the depositing of enamels and adhesive to its surface.

Other applications of the invention can be made, particularly in the field of printed circuits, making it possible similarly to determine the thicknesses of the layers of inks deposited, the presence of unwanted oxides, etc.

BRIEF DESCRIPTION OF THE DRAWINGS

This invention will now be described by way of non-limiting example with regard to FIGS. 1 to 3 which relate respectively.

DETAILED DESCRIPTION OF THE PREFERRED EMBODIMENTS

Figure 1:
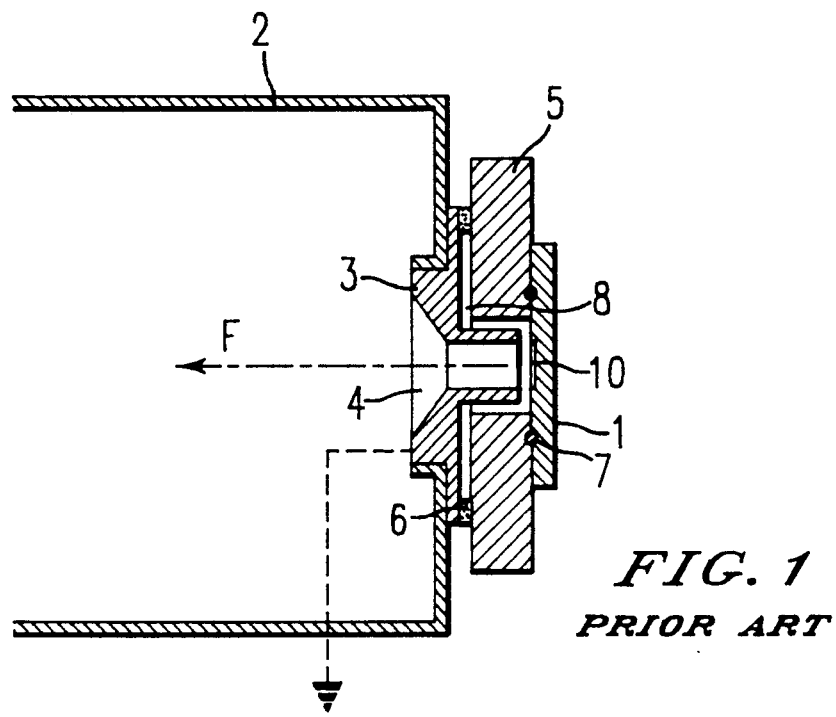
FIG. 1 is to a diagram of a device for using an LDS according to the prior art.

With reference to FIG. 1, the diagram is seen of a Grimm lamp used for the LDS process applied previously to the analysis of the conductive surfaces of a sample 1.

It is essentially consists of an enclosure 2 containing argon under slight pressure.

At one of its ends an anode 3 of copper alloy is grounded and provided with a central opening 4. A cathode 5 is opposite it and supports conductive sample 1; it is brought to a potential of $-400$ to $-2000$ volts. Seals 6–7 assure fluidtightness between the preceding elements. A spacing 8 on the order of 0.15 mm exists between electrodes 3–5; it is subjected to a vacuum greater than that of enclosure 2 so as to avoid the creation of discharges therein and, on the contrary, to facilitate their concentration, opposite sample 1.

In operation, the bombarding of zone 10 of the sample by argon $Ar^+$ ions breaks loose atoms which constitute it; these atoms, excited by secondary impacts emit —while finding a stable level —a characteristic radiation, a fraction of which is directed along arrow F, then analyzed by a spectrometer, not shown, thereby continuously delivering qualitative and quantitative data pertaining to sample 1.

Figure 2:
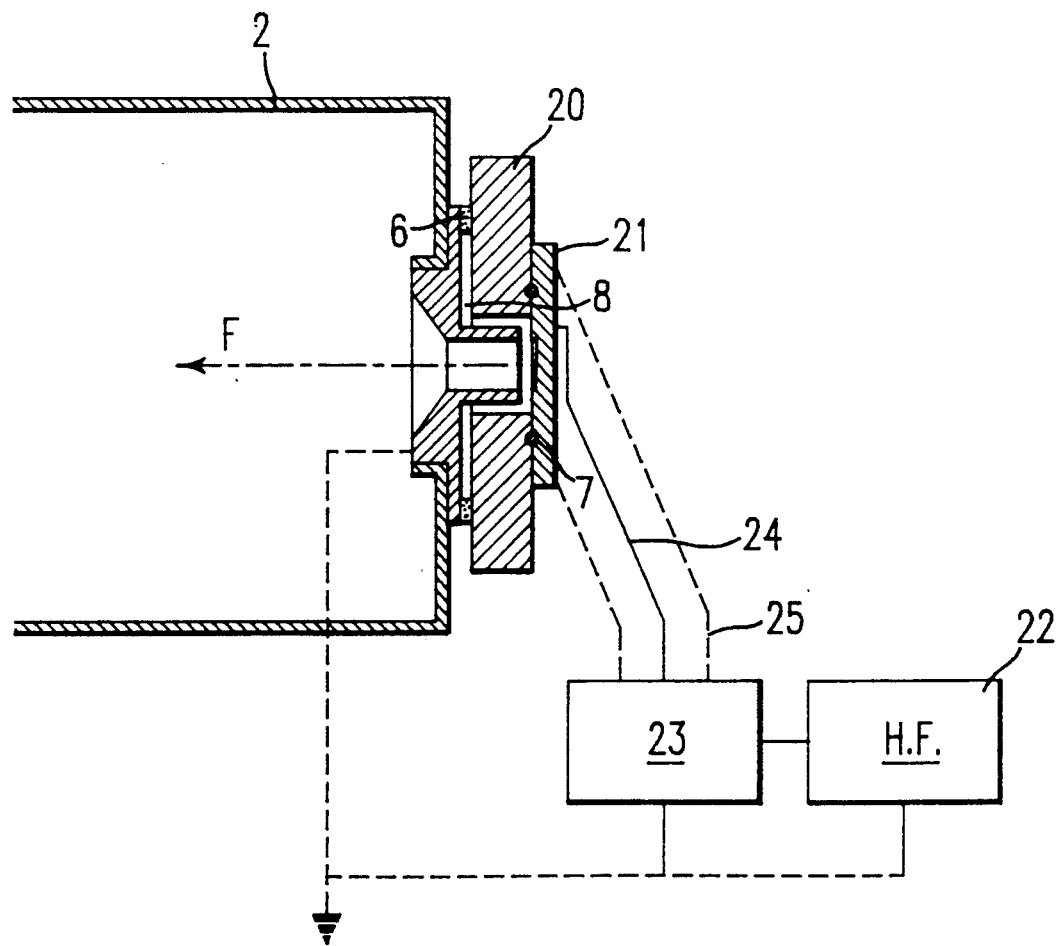
FIG. 2 is to a similar diagram according to the invention.

FIG. 2 represents the modification of the device of FIG. 1, for using the device according to the invention.

As in the preceding case, there are the enclosure containing argon at low pressure, anode 3 separated from cathode 20 by the spacing, seals 6 and 7 assuring the fluidtightness respectively between electrodes 3–20 and nonconductive sample 21. The latter is connected to a high-frequency current generator 22 by an adapter 23 and a strip 24, surrounded by a shielding 25 to avoid the interference of the electronic environment.

Figure 3:
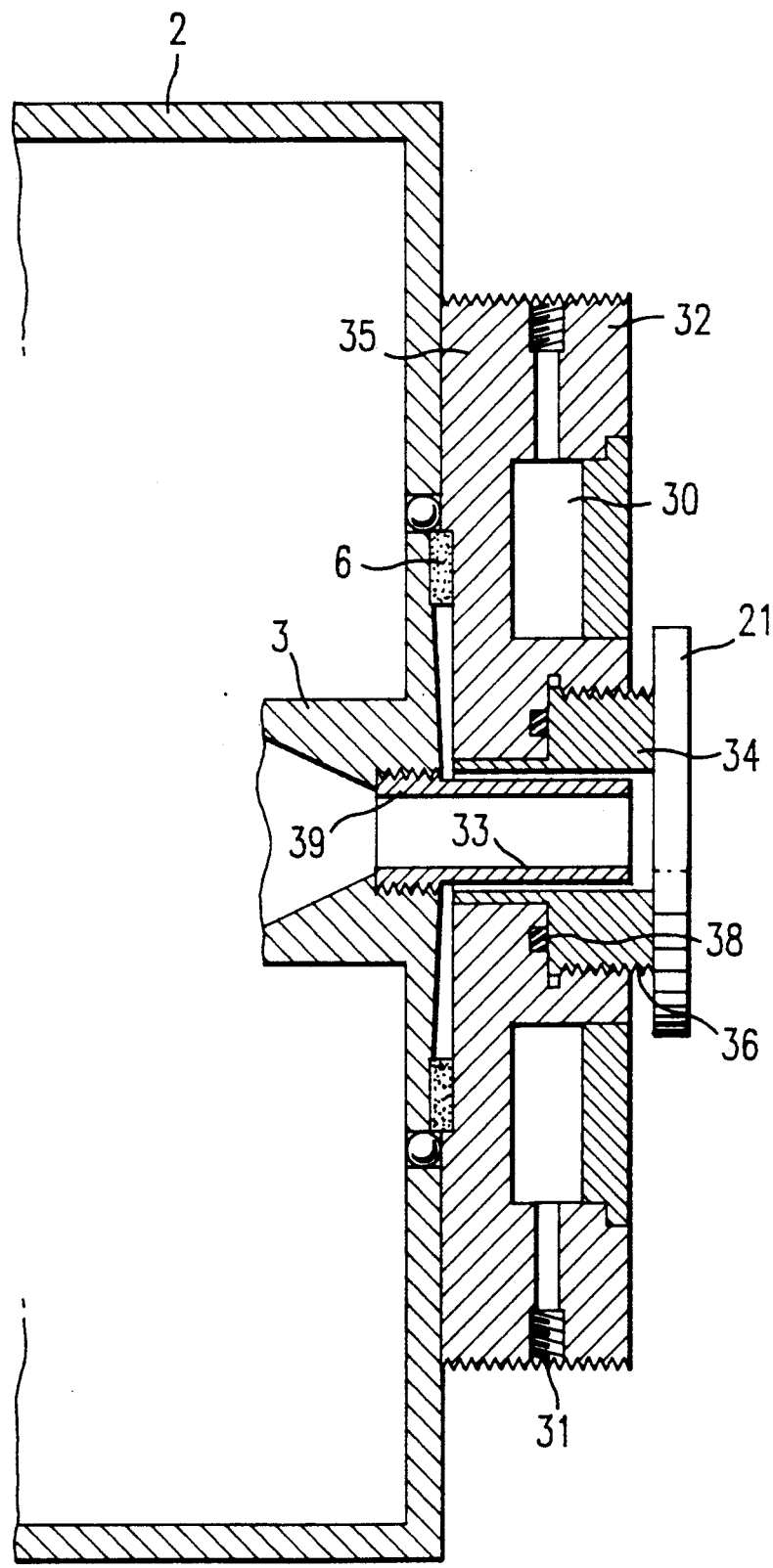
FIG. 3 is to a detail view in section of the anode-cathode assembly of FIG. 2.

The modification is essentially concerned with cathode 20, that can.be seen better in detail in FIG. 3, and with the use of an HF current power supply source 22 that makes possible the analysis of a nonconductive sample 21.

It is known that this latter, when it is subjected to a continuous negative potential according to the prior art, will be charged positively under the effect of a bombardment of positive argon ions: consequently, it will quickly develop a repulsion barrier making impossible the subsequent passage of current and, therefore, any analyzable emission of its constituents.

On the other hand, if a high-frequency (HF) alternating voltage is applied to the sample, it is propagated at its surface by skin effect and renders it negative by self-bias phenomenon.

Its principle is as follows:

At each alternation of the current, the surface of sample 21 is bombarded by $Ar^+$ ions and by electrons; however, since the mobility of the latter is much higher (on the order or $10^5$ times), the surface will absorb more electrons, hence its resultant negative charge. The latter, therefore, attracts the incident $Ar^+$ ions that bombard it, erode it and free the analyzable constituents from it. Therefore, we are again under the conditions of the LDS process applied to the conductive samples, thus making possible the investigation of gradients of compositions of said nonconductive samples 21.

By way of example, the LDS device of FIG. 1 has been modified in the sense of FIG. 2 by the use of an HF generator 422 of the ARG 500 ALCATEL type, combined with a SIEMENS/SOCABIM acquisition system with a capacity of 30,000 measurements/sec. An RSV type ANALYMAT 2,500 spectrometer can be used jointly. The power used is on the order of 30 to 100 watts and the frequency preferably 13.56 MHz.

In addition to the power supply, the invention also is concerned with the structure of cathode 20 that is seen in detail in FIG. 3. Its originality resides in the fact that it is composite; it remains, in part, identical with the cathode used for the standard LDS.

Its body 35 is essentially of copper alloy; it comprises a circulation duct 30-31 for cooling fluid, and its periphery 32 is threaded to make possible the fastening of a ring, not shown, supporting various accompanying elements such as means for holding sample 21 and for periodic cleaning of inner part 23 of anode 3 already present in this standard LDS device.

The cathode according to the invention, however, differs from the one (1) of FIG. 1 in that its central part 40 comprises a removable part 34. The latter is made solid in the main body 35 by screwing into a bore 36 drilled about half-way through the thickness of the cathode.

Removable part 34 is of an insulating material such as a ceramic and has an outside diameter less than that of sample 21 to be analyzed; for example, these latter can be respectively on the order of 20 and 30 mm;, respectively its inner part consists of a tube whose length corresponds to the thickness of cathode 35.

Furthermore, it exhibits an excess thickness of several mm sufficient to prevent any electric contact between sample 21 and main body 35 of the cathode; an O-ring 38 assures the fluidtightness between these two elements.

It will be noted that central part 39 of anode 3 can also be removable, which makes it possible to change the pair 33-34 and to adapt it to the need of the analysis, particularly to the dimensions of samples 21 which can thereby have more or less large diameters, without changing the entire cathode.

The arrangement that has just been described exhibits many advantages:

The HF current is concentrated in the sole ceramic portion 34 of slight diameter; this allows a weaker power from the generator and an easier adjustment of the device, especially its impedance, which would not be the case if the entire cathode 32 were of copper; moreover, considering the fragility of the ceramic and the difficulties to work it, the fastening on its periphery of the accompanying elements already mentioned would be a source of major technical difficulties.

The use of parts 34 of small diameter makes possible the study of small parts, avoiding defects of surface evenness and locating precisely the defects to be analyzed, frequently marked by spots.

The easy removal of the pair consisting of central part 39 of the anode and ceramic element 34 makes it possible, in addition to a change in dimension, to allow also a change of material, and for example to return to the standard LDS system by using elements of a copper alloy. Thus, with the same set of materials it is possible easily to use one technique or the other; the passage of the analysis from a conductive material to a nonconductive material is, under these conditions, very quick, because it actually involves no complete removal of the Grimm lamp, or consecutive meticulous adjusting of the concentricity of the elements, the parallelism of the electrodes, or laying down of the accompanying elements, etc.

We claim:

1. Process of analysis of surfaces of a sample by luminescent discharge spectrometry using an anode and a cathode, comprising the steps of:
    applying a high frequency current to be used for the creation of a discharge between the anode and the cathode onto a nonconductive sample to be analyzed; and
    permitting the current to be propagated on said sample by skin effect.

2. Process according to claim 1, wherein said high frequency current has a power on the order of 30 to 100 watts and a frequency on the order of 13.56 MHz.

3. Device for using the process of claim 1, comprising an enclosure on which is mounted an anode and a cathode supporting a sample, wherein the sample to be analyzed is connected to a high-frequency generator.

4. Device according to claim 3, wherein the cathode is formed of a copper alloy body and a removable central part of an insulating ceramic, said central part having an outside diameter less than that of the sample to be analyzed and extending from the body of the cathode to prevent any electric contact between the body of the cathode and the sample, said central part having a length which corresponds to the thickness of the cathode.

5. Device according to claim 4, wherein a central part of said anode is removable and with said central part of the cathode constitutes an adjusted pair that can be replaced simultaneously with another pair differing from it by the outer dimensions of the cathode or the nature of the material thereof.

6. Device according to claim 4, wherein the removable central part of the cathode is screwed into a corresponding bore placed in the body of the cathode, by approximately half of the thickness of the cathode.

* * * * *